United States Patent [19]
Loucas

[11] Patent Number: 5,368,866
[45] Date of Patent: Nov. 29, 1994

[54] DEER REPELLENT COMPOSITION, PROCESS FOR MAKING SAME, AND A TREATMENT METHOD FOR APPLYING THE SAME

[76] Inventor: Athena P. Loucas, 58 High Valley Way, Stamford, Conn. 06903

[21] Appl. No.: 142,612

[22] Filed: Oct. 25, 1993

[51] Int. Cl.⁵ .................. A01N 25/24; A01N 37/18; A61K 31/16
[52] U.S. Cl. .................. 424/581; 424/405; 424/407; 514/626; 514/627
[58] Field of Search .............. 424/581, 405, 407; 514/626, 627

[56] References Cited

U.S. PATENT DOCUMENTS 4,775,532 10/1988 Clayton ........................ 424/195.1
5,178,879 1/1993 Adekunle et al. .............. 424/484

Primary Examiner—Douglas W. Robinson
Assistant Examiner—L. Blaine Lankford
Attorney, Agent, or Firm—Galgano & Burke

[57] ABSTRACT

A deer repellent composition for the protection of vegetation includes an active ingredient comprising egg and a red hot sauce, composed of pepper, vinegar, garlic, salt and water; a carrier; and a diluent. The vegetation is protected by applying an effective amount of the composition thereto, preferably by spraying. The composition may include the aforementioned ingredients in the following percentages: about 3-7 percent eggs; about 6-19 percent red hot sauce; about 3-7 percent carrier; and about 68-91 percent diluent, the total composition equaling 100 percent by weight. A process for preparing the mixture is also enclosed.

1 Claim, No Drawings

DEER REPELLENT COMPOSITION, PROCESS FOR MAKING SAME, AND A TREATMENT METHOD FOR APPLYING THE SAME

BACKGROUND OF THE INVENTION

The present invention relates to a deer repellent composition and a treatment method for protecting vegetation (i.e., plants, flowers, food crops, shrubs, trees and the like) from deer. In particular, the present invention relates to an all natural deer repellent which is not harmful to humans, animals or the environment.

When one is attempting to grow a flower or vegetable garden, the presence of deer can develop into a terrible nuisance, as they will usually eat the entire garden, unless it is protected by fencing, or the like. Many people have tried various repellents and home remedies, e.g., human hair, dried blood, garlic, soap, along with commercial chemical solutions. All of these methods have generally failed. Some of them must be constantly renewed (i.e., renewed every two weeks or so), and the chemical solutions employed have contributed to environmental pollution.

SUMMARY OF THE INVENTION

Accordingly, it is an object of the present invention to provide a novel deer repellent composition which is all natural, does not contain any toxic chemicals and is completely biodegradable.

It is a further object of the present invention to provide such a novel deer repellent solution which produces an odor and taste factor which is offensive to animals, but is sufficiently mild so as not to bother humans.

It is a more particular object of the present invention to provide such a novel repellent which can be easily sprayed onto all types of vegetation, e.g., flowers, plants, food crops, bushes and trees for protection against deer.

It is a more particular object of the present invention to provide such a novel deer repellent which will protect vegetation, but will not be harmful to the deer, humans and the environment, and to provide such a composition which is long-lasting.

Certain of the foregoing and related objects are readily attained in a deer repellent composition for the protection of vegetation, comprising an active ingredient comprising egg and red hot sauce; a carrier; and a diluent.

Preferably, the carrier is a non-toxic glue and the diluent is water. The red hot sauce preferably consists of cayenne peppers, vinegar, garlic, salt and water.

In a preferred embodiment of the invention, the composition comprises about 3-7 percent eggs; about 6-19 percent red hot sauce; about 3-7 percent carrier; and about 68-91 percent diluent, the total composition equaling 100 percent by weight.

Certain of the foregoing and related objects are also attained via a method for protecting vegetation, from deer, comprising the steps of applying to said vegetation an effective amount of the aforementioned deer repellent composition. Most advantageously, the application is effected by spraying.

Certain of the foregoing and related objects are also attained via a process for protecting vegetation from deer comprising the steps of blending an egg, mixing glue with the blended egg, adding boiling water to the blended egg and glue, further adding red hot sauce to the blended egg, glue and water mixture, and finally adding water to the mixture.

DETAILED DESCRIPTION OF THE PREFERRED EMBODIMENT

In accordance with the present invention, the deer repellent composition includes the following ingredients: about 1-2 eggs (about 3-7 percent); about 2-6 ounces of red hot sauce (about 6-19 percent); about 1-2 ounces of a carrier, such as an adherent, non-toxic glue (about 3-7 percent); and a diluent, e.g., water, added to produce a total of approximately 32 ounces (about 68 percent added to equal 100 percent by weight). Preferably, the composition includes the following ingredients: 1 jumbo egg (2 ounces); red hot sauce (4 ounces); a non-toxic adherent glue (1 ounce); and a diluent, water (25 ounces).

In use, one would spray the deer repellent composition on the desired vegetation, e.g., flowers, plants, bushes and trees, etc., for protection against deer; as used herein, "vegetation" refers to all types of plants, shrubbery, trees, bushes, flowers, crops, etc., which attract deer. It can be used in the spraying on new plants and flowers. It can also be used in the summer for flowers and new growth. For the fall, it would be used on bushes and fall flowers. In the winter, it can be used to protect evergreens. For best results, it should be sprayed on the vegetation from a variety of angles to ensure complete coverage and protection, preferably when the leaves are dry, when there is little or no wind, and when the temperature is above 40° F. It should be stored in a cool place or refrigerated.

The hot sauce used is that made by Durkee Famous Foods, SCM Corporation of Westlake, Ohio, the ingredients of which consist of aged red or cayenne peppers, vinegar, water, salt and garlic; the pepper and garlic provide the most taste and odor. Other commercial red hot sauces can also be employed.

The glue employed may comprise any commercially EPA approved, non-toxic water soluble glue such as that made by Borden, Inc., of Columbus, Ohio, identified as Elmer's Glue; or that made by Franklin International, of Columbus, Ohio, identified as Titebond Wood Glue. Both products are non-toxic (as defined in the Federal Hazardous Substances Act), water soluble, and environmentally safe. Other commercial nontoxic, water soluble glues can be used, provided they serve to adhere the active ingredient to the vegetation.

The composition is prepared by initially adding to a blender one egg. Then the glue and 2 ounces of boiling water are added, and the ingredients are mixed well. Then the red hot sauce is added and mixed with the previously-added ingredients. Finally, the remaining 23 ounces of cold water are added and mixed, and the mixed composition is poured into a spray bottle, preferably of the pump-action type.

The composition could also be sold in a 32 ounce concentrate, preferably comprised of: 8 ounces of eggs (approximately 4 jumbo eggs); 16 ounces of red hot sauce; 4 ounces of glue; and 4 ounces of water. Prior to use, the customer would simply further dilute the concentrate with water.

One thorough application of the invention deer repellent lasts two to three months; however, the composition must be applied on new flowers and new growth as they appear because the deer will test the planting and eat whatever has not been sprayed. It is especially important in the spring to spray often to prevent the new growth from being eaten. Severe weather conditions also require frequent spraying (i.e., "often" can be defined as every week or every 10 days, depending on the rate of growth of the plant). Because it may change the taste of edible crops slightly, it is preferable that the invention composition be sprayed around, but not directly on those crops.

The invention will now be described in greater detail by means of the following examples. It should be stressed, however, that the examples are provided for purposes of illustration, rather than as a definition of the limits or scope of the present invention.

EXAMPLE 1

Two bushes of similar size and type located near each other were picked as test samples. One bush was sprayed with the invention composition, the other was not sprayed. The results were that the treated bush was twice the size and had a full growth of leaves at the end of the test, three months later. The untreated bush was half the size and had very few leaves—most of which were partially or totally eaten by deer.

EXAMPLE 2

A lily bed of various shades of day lilies was divided in half. (The bed is oval-shaped and approximately 12' by 6'.) Side A was sprayed with the invention formula, and Side B was not sprayed. As new growth appeared on Side A, the invention formula was re-applied. Side A produced plants and flowers. Side B had very few plants that developed, since the deer ate the plant before it had a chance to produce any flowers.

EXAMPLE 3

Impatiens beds were planted in strategic areas of the garden where deer normally wander by (along the driveway, away from the house and other plants, in the forest area, alongside hosta (one of their favorite plants), in the herb beds and in planters strategically placed where the deer wander. The impatiens that were treated with the invention composition remained untouched, as opposed to the untreated plants (located right next to them) that were chewed down to the ground.

EXAMPLE 4

Similar tests were conducted with tulips, roses, yew, rhododendron, azalea, etc. Positive results were obtained using the invention formula in all instances.

EXAMPLE 5

Untreated rhododendron bushes that are four to six feet tall were bare from the middle of the plant down to the ground, due to being attacked by deer. (They had leaves and flowers above the average reach of the deer.) When the bottom branches were sprayed with the invention formula, these bottom branches produced leaves growing, and were no longer bare.

Thus, while only a few examples of the present invention have been shown and described, it is to be understood that many changes and modifications may be made thereunto without departing from the spirit and scope of the invention as disclosed herein.

What is claimed is:

1. A natural, non-toxic deer repellent composition for the protection of vegetation, comprising:
   an active ingredient of egg and cayenne pepper sauce;
   a non-toxic glue on the carrier; and
   a diluent.

* * * * *